United States Patent [19]

Brunke et al.

[11] Patent Number: 4,582,945

[45] Date of Patent: Apr. 15, 1986

[54] C-8-SUBSTITUTED 1,5-DIMETHYL-BICYCLO[3.2.1]OCTANE-8-OLS

[75] Inventors: Ernst-Joachim Brunke; Hartmut Struwe, both of Holzminden, Fed. Rep. of Germany

[73] Assignee: Dragoco Gerberding & Co. GmbH, Holzminden, Fed. Rep. of Germany

[21] Appl. No.: 400,262

[22] Filed: Jul. 21, 1982

[30] Foreign Application Priority Data

Jul. 21, 1981 [DE] Fed. Rep. of Germany ....... 3128790

[51] Int. Cl.$^4$ ...................... C07C 35/22; C07C 35/31
[52] U.S. Cl. .................. 568/820; 252/522 R; 568/819
[58] Field of Search ................ 568/819, 820, 821; 252/522 R, 522

[56] References Cited

U.S. PATENT DOCUMENTS

4,237,322 12/1980 Mulder et al. ...................... 568/820
4,248,742 2/1981 Escher et al. ...................... 568/820

FOREIGN PATENT DOCUMENTS

0070566 1/1983 European Pat. Off. ............ 568/820
0074543 3/1983 European Pat. Off. ............ 568/820
2020659 11/1979 United Kingdom ................ 568/820

OTHER PUBLICATIONS

Marshall et al., "J. Org. Chem." vol. 33, p. 2593 (1968).
Ayer et al., "Canadian J. Chem." vol. 54, p. 3276 (1976).
Whitesell et al., "Tetrahdedron Letters" pp. 1549–1552 (1976).
Goering et al., "J. Amer. Chem. Soc." vol. 83, (1961), pp. 1391–1401.
Nedenskov et al., "Acta Chem. Scand." vol. 16, pp. 246–248 (1962).
Brunke et al., "Chem. Abst. vol. 98, (1983), p. 160298(e).

Primary Examiner—Werren B. Lone
Attorney, Agent, or Firm—Anthony J. Casella; Gerald E. Hespos

[57] ABSTRACT

C-8-substituted 1,5-dimethyl-bicyclo[3.2.1]octane-8-ols having the general formula I

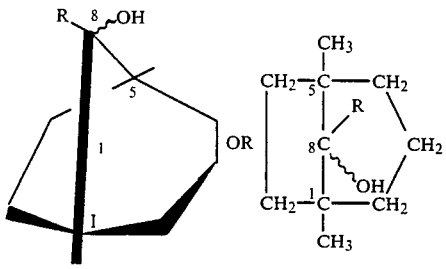

wherein R is a lower open chained or cyclic alkyl- alkenyl- or alkinyl group having up to 6 carbon atoms and the wavy line at the C-8 atom means epimeric forms, the process for producing these compounds and their use as odorants and constituents of parfume composition for cosmetic and industrial parfuming or essential oils and flavoring agents.

16 Claims, 1 Drawing Figure

7: R = Ethyl        12: R = 1-Methyl-propyl
8: R = Methyl       13: R = 2-Methyl-propyl
9: R = n-Propyl     14: R = Allyl
10: R = i-Propyl    15: R = n-Hexyl
11: R = n-Butyl     16: R = 3-Methyl-butyl
                    17: R = Cyclopentyl
                    18: R = Cyclohexyl

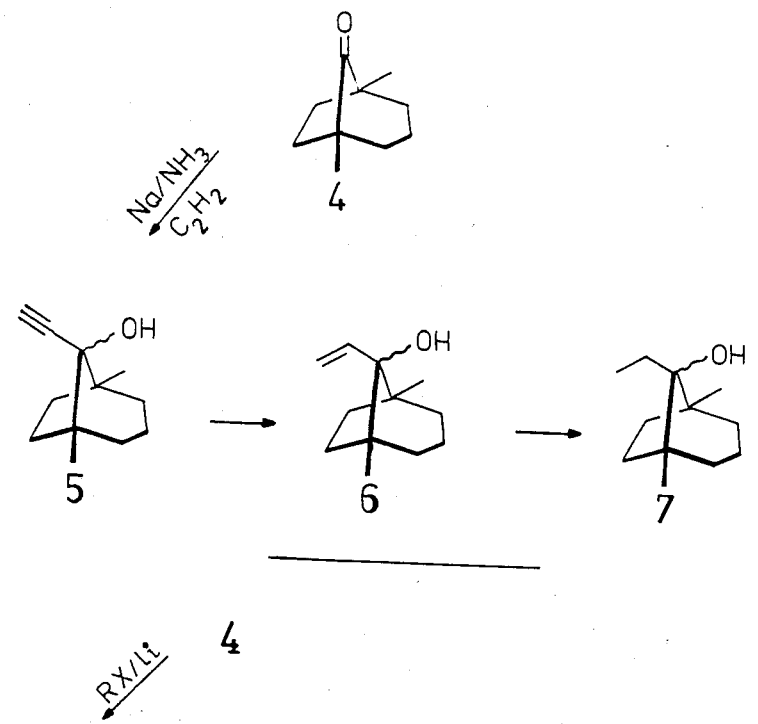
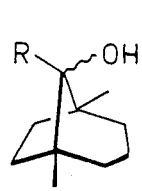
7: R = Ethyl        12: R = 1-Methyl-propyl
8: R = Methyl       13: R = 2-Methyl-propyl
9: R = n-Propyl     14: R = Allyl
10: R = i-Propyl    15: R = n-Hexyl
11: R = n-Butyl     16: R = 3-Methyl-butyl
                    17: R = Cyclopentyl
                    18: R = Cyclohexyl

C-8-SUBSTITUTED 1,5-DIMETHYL-BICYCLO[3.2.1]OCTANE-8-OLS

THE INVENTION

The invention relates to novel 1,5-dimethyl-bicyclo[3.2.1]octane-8-ols substituted at the C-8 atom and having the general Formula I, wherein R is a lower straight chained or branched alkyl, alkenyl or alkinyl residue having up to 6 C-atoms and the wavy line at the C-8 atom means epimeric forms

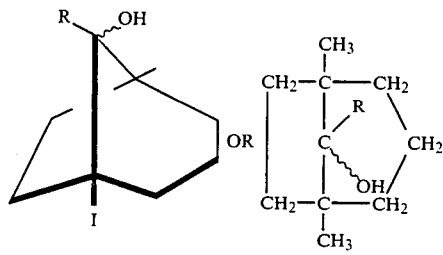

Furthermore the invention relates to the process of producing the compounds of general formula I as well as their use as odorants and thus also parfume compositions which are characterized by a contents of a compound of general formula I.

It has been found that the novel 1,5-dimethyl-bicyclo[3.2.1]octane-8-ols substituted at the C-8 atom and having the general formula I are valuable and stable odorants. The compounds of general formula I have earthy, woody and fresh notes, some of which have an extremly strong odor intensity.

BRIEF DESCRIPTION OF THE DRAWING

FIG. I is a flow sheet showing the preparation of compounds of the invention.

BACKGROUND OF THE INVENTION

The perfume industry has used patchouli oil for many years. This essential oil of Pogostemon patchouly has a distinctive woody-earthy odor complex and a diffusive effect, which develops particularly in perfume compositions. Patchoulol (A) and norpatchoulenol (B) have been described as the constituents of patchouli oil with the greatest olfactory significance. No syntheses of A and B for industrial use are known.

The geosmin (C) produced by microorganisms causes the odor of fresh earth. As had been demonstrated on the basis of synthesized geosmin, this substance has one of the highest odor intensities known. The use of a mixture of geosmin stereoisomers in perfume compositions has been described in U.S. Pat. No. 4,248,742. This isomer mixture was prepared in accordance with the method of Marshall et al. (J. Org. Chem. 33, 2593 (1968)) and Ayer et al. (Canad. J. Chem. 54, 3276 (1976)). However, this method is not used in industry.

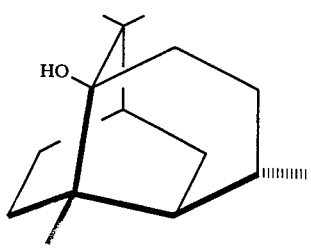

A

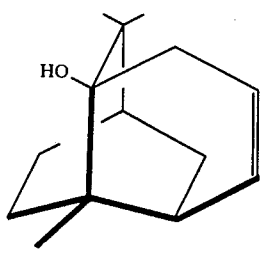

B

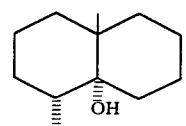

C

The sometimes limited availability of patchouli oil and its highly variable odor quality and the non-availability of geosmin are reasons for developing synthetic odorants producing one or more of the olfactory aspects of patchouli oil or of geosmin. It is an object of the invention to manufacture such perfume agents in the required amounts with a consistent odor quality.

A series of uniform perfuming agents have been previously available, whose odor consists of a combination of earthy and camphorous aspects. Perfuming agents with distinct campher notes have only limited applications in the perfume industry, and are not, for instance, suitable substitutes for patchouli.

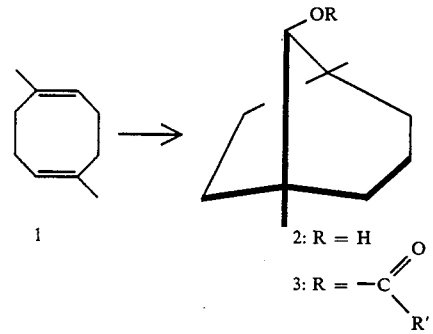

The secondary alcohol 2 with a 1.5-dimethyl-bicyclo[3.2.1]octan framework, whose preparation from 1.5-dimethyl-1.5-cyclooctadien (1) has been described by I. K. Whitesell et al. (Tetrahedron Letters, 1976, p. 1549–1552) and A. I. Mulder and A. I. de Jong (UK Pat. Application No. 2020659A), has an unpleasant medicinal camphor odor. UK Pat. Application No. 2020659A claims esters 3 (R'=Me, Et, Pr, . . . ) of alcohol 2 as perfuming agents, since unlike 2 they possess pleasant flowery, spicy and woody notes.

DE-OS No. 2 945 812 describes the oxidation of 2 which produces ketone 4; according to this publication, 4 possesses an odor of conifers and camphor with a spicy note. The same DE-OS describes acetales 5 prepared from 4 which have camphor-like notes plus eucalyptus-, rosemary- and rose-like notes.

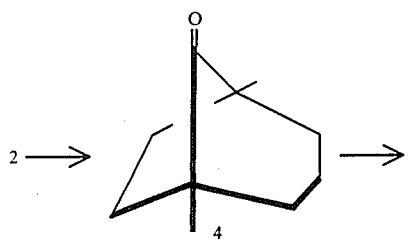

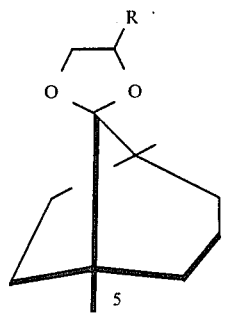

The ethylene glycol acetal has a borneol-like odor with a weak earthy side note (also when R=H).

PREFERRED EMBODIMENTS OF THE INVENTION

It was a surprise to discover that the novel tertiary alcohols with the general formula I prepared from 4 have a natural-smelling earthy odor with a very great olfactory intensity. Additional woody side notes occur in some derivatives, which is definitely desirable in the perfume industry. A typical comphorous odor is only observed in a few compounds. The compounds which are the subject of this invention with the general formula I can thus be used as perfuming agents and may be used to very good effect in perfume compositions. The stability of compounds with the general formula I permits their use in perfuming chemically aggressive media.

The earthy notes of compounds with the general formula I may also be of advantage in the reconstruction of essential oils or flavoring concentrates, to which they confer a natural effect even in very small dosages.

Compounds with the general formula I are produced in the known way by converting 1.5-dimethyl-bicyclo[3.2.1]octane-8-on (3) with metal-organic compounds. Thus addition of metallized acetylene, preferably using potassium hydroxide in n-butanol/dimethyl formamide produces the ethinyl carbinol 5, which by means of selective hydrogenation, preferably using a Lindlar catalyst, leads to the vinyl carbinol 6 or, by means of complete hydrogenation preferably using Raney-Nickel, leads to the ethyl derivative 7. Apart from these preferred reaction conditions, other chemical methods and processes are known which lead to the substances 5, 6 and 7 which are the subject of the invention. The addition of acetylene can be carried out using sodium or lithium amide in liquid ammonium, and the hydrogenation to 7 may be carried out using various noble metal catalysts.

Carbinols 8–18 were preferably obtained by converting 4 with the appropriate lithium-organic compounds (R—Li) followed by hydrolysis. The preferred solvents were diethyl ether or tetrahydrofuran. The reaction temperatures preferably lay between room temperature and boiling point and the reaction times for 0.3 molar batches between 1 and 3 hours. When performing Grignard reactions with keton 4, substantial amounts of the secondary alcohol 2 were always obtained in addition to the desired tertiary carbinols 7–18 as the product of a Grignard reaction.

TABLE 1

| | Mass Spectrometry Data of Compounds of General Formula I % based on Basepeak | | | | |
|---|---|---|---|---|---|
| R | $M^+$ | $[M - 18]^+$ | $[M - R]^+$ m/z 153 | $[M - (R + 18)]^+$ m/z 135 | $R^+$ |
| methyl- | 33 | 27 | 28 | 46 | no reading |
| ethyl- | 2 | 2 | 100 | 56 | 19 |
| n-propyl- | 2 | 2 | 100 | 67 | 50 |
| isopropyl- | 3 | — | 50 | 54 | 100 |
| n-butyl- | 2 | 1 | 100 | 61 | 20 |
| isobutyl- | 6 | 2 | 100 | 72 | 38 |
| sec.-butyl- | 6 | — | 61 | 77 | 51 |
| isoamyl- | 2 | 1 | 100 | 47 | 12 |
| cyclopentyl- | 6 | 1 | 61 | 48 | 100 |
| hexyl- | 2 | 1 | 100 | 44 | 6 |
| cyclohexyl- | 3 | — | 100 | 59 | 50 |
| vinyl- | 5 | 3 | 1 | 3 | 46 |
| ethinyl- | 1 | 1 | 1 | 100 | no reading |

The structures of the novel compounds of formula I are spectroscopically characterized by infrared, $^1$H-NMR as well as mass spectra (see also examples 1 to 7). The relatively small molepeak as well as the $[M-18]^+$-peak resulting by splitting off water may be evidenced by mass spectrometry. The fraction having m/z=153 and resulting from splitting off the residue at the C-8 atom is significant for compounds having a saturated residue on the C-8 atom. The fragment ion $R^+$ resulting from this residue may always be evidenced (except in 7). Also the fragment ion m/z=135, resulting by splitting off water and the C-8 residues is also pronounced (see table 1). Constitution of the novel compounds is characterized by the $^1$H-NMR-signal at 0.90 ppm/6H for both methyl groups.

TABLE 2

| | Odor description of carbinols 5–18 (1% in ethanol) | |
|---|---|---|
| Compound | Odor evaluation after 5 min | Odor evaluation after 2 hours |
| 5 | (very intense) pleasantly earthy, naturally fresh | odorless |
| 6 | (very intense) fresh-earthy slightly camphorous | odorless |
| 7 | (extremely intense) natural fresh-earthy | odorless |
| 8 | (extremely intense) earthy, mouldy | odorless |
| 9 | (medium intensity) distinctly | weak woody |

TABLE 2-continued

| | Odor description of carbinols 5-18 (1% in ethanol) | |
|---|---|---|
| Compound | Odor evaluation after 5 min | Odor evaluation after 2 hours |
| | earthy-camphorous, slightly herbal, fresh | |
| 10 | (very intense) earthy, slightly woody | woody-earthy |
| 11 | (relatively weak) distinctly earthy-camphorous (similar to 9 but slightly weaker) | slightly woody |
| 12 | (relatively weak) earthy-woody | very slightly woody |
| 13 | (medium intensity) earthy, slightly woody (similar to 10 but slightly stronger woody aspect) | slightly woody |
| 14 | (very intense) typically camphorous, earthy | clearly of the same type |
| 15 | very weak | almost odorless |
| 16 | (medium intensity) labdanum note leathery | weak woody |
| 17 | (medium intensity) earthy, distinctly woody (similar to 10) | woody |
| 18 | (relatively weak) lightly camphorous-woody | very weak woody |

The odor characteristics of compounds 5 to 18 were obtained by a team of experts (see table 2). Although all of the quoted compounds have noticeable olfactory characteristics, which may permit industrial applications, the compounds of formula I where R=methyl, ethyl, iso-propyl, vinyl or ethinyl are to be stressed as especially interesting. These substances have a considerable odor intensity and cause clear and very desirable effects when incorporated in perfume oils, even in very small dosages. This is demonstrated in Examples 8 and 9.

The corresponding esters having lower alkyl residues were prepared from alcohols 5 to 18 by conventional esterifying reactions. These esters, especially the acetates, have woody, earthy as well as green notes of relatively low intensity. It may be assumed that traces of the corresponding alcohols having more intense odor mask the actual odor of the esters.

The invention is better illustrated by but not limited to the following examples:

EXAMPLE 1

1.5-dimethyl-8-ethinyl-bicyclo[3.2.1]octane-8-ol (5)

To a suspension of 79.6 g KOH (powdered) in 17.3 ml n-butanole and 32 ml benzene, 21.6 ml N,N-dimethylformamide were added dropwise at 10° C. Then gaseous acetylene (washed with conc. $H_2SO_4$) was passed in for about 1 hour under rigorous stirring. While continuously passing in acetylene 76 g (0,5 mole) 4 were dripped in within 30 min. After 30 min. of stirring at 10° C. 100 ml water were added for hydrolysis and isolation. The raw product (about 88 g) was destilled over a turning band column which resulted in 64 g (72%) of 5 having a boiling point (1 mm) of 60° C. The product solidified to a colorless cristalline mass having a melting point of 33° to 35° C.—IR: 3500 (O—H); 3300, 2100 cm$^{-1}$ (—C≡C—H).—NMR (CCl$_4$): δ=1.05 s (1-, 5-CH$_3$), 1.5, br.s (6-, 7-CH$_2$), 2.42 ppm, s (—C≡C—H).$C_{12}H_{18}O$ (M=178,26).

EXAMPLE 2

1,5-dimethyl-8-vinyle-bicyclo[3.2.1]octane-8-ol (6)

A solution of 53.4 g (0.3 mole) 5 in 150 ml benzene was mixed with 500 mg Lindlar catalyst and shaken under a hydrogen atmosphere (normal conditions of pressure and temperature). After absorbing one equivalent $H_2$ (6.72 l) the reaction medium was filtered, evaporated and destilled. This resulted in 46 g (84%) 6 in form of colorless oil having a boiling point (1 mm) of 70° C. IR: 3500/3600 (O—H), 3080, 1635, 990, 910 cm$^{-1}$ (—CH=CH$_2$).—NMR (CCl$_4$): δ=0.75, s (1-, 5-CH$_3$), 1.50/1.53, br.s (6-, 7-CH$_2$), 5.0–6.2 ppm (—C$\underline{H}$=C$\underline{H}_2$).$C_{12}H_{20}O$ (M=180,28).

EXAMPLE 3

1.5-dimethyl-8-ethyl-bicyclo[3.2.1]octane-8-ol (7)

A solution of 178 g (1 mole) 5 in 1000 ml destilled methanole was mixed with 1 g Raney nickel and hydrogenated in an autoclave (20 bar/20° to 30° C.). After about 4 h the uptake of hydrogen was finished (2 equivalents H$_2$). The reaction mixture was taken from the autoclave, filtered, evaporated and distilled. This resulted in 155 g (85%) of 7 in form of a colorless oil having a boiling point (1 mm) of 68° C. IR: 3500/3600 cm$^{-1}$ (O—H).—NMR (CCl$_4$): δ=0.88, s (1-, 5-CH$_2$), 0.97, t, J=7 Hz (—CH$_2$—CH$_3$), 1.45 ppm, br.s (6-, 7-CH$_2$).—MS: m/e (%)=153 (100, M+-29), 135 (56), 125 (20), 123 (20), 107 (71), 99 (20), 95 (45), 69 (46).$C_{12}H_{22}O$ (M=182.30).

EXAMPLE 4

1,5,8-trimethyl-bicyclo[3.2.1]octane-8-ol (8)

To a solution of 45,8 g (0,3 mole) of 1,5-dimethyl-bicyclo[3.2.1]octane-8-one in 150 ml dried dimethylether at boiling temperature 250 ml (178 g) of a 5% solution of methyl lithium (4 mole) in diethylether were dropwise added under stirring. After 1 h of stirring at boiling temperature about 50 ml water were dripped in followed by extraction with diethylether. The combined organic phases were dried over Na$_2$SO$_4$, evaporated under vacuum and distilled which resulted in 37 g (73%) of 8 in form of a colorless oil having a boiling point (1 mm) of 74° C. IR (as oil film): 3500 cm$^{-1}$ (O—H).—NMR (CCl$_4$): δ=0,87, s, 6H (1,5-CH$_3$), 1,05, s, 3H (8-CH$_3$) 1.5 ppm, br.s, 4H (6,7-CH$_2$).—MS: m/e (%)=168 (33, M+), 153 (28), 150 (29), 135 (46), 125 (30), 124 (18), 123 (31), 122 (20), 121 (42), 111 (11), 110 (10), 109 (16), 108 (19), 107 (85), . . . , 43 (100).$C_{11}H_{20}O$ (M=168,27).

EXAMPLE 5

1,5-dimehtyl-8-ethyl-bicyclo[3.2.1]octane-8-ol (7)

A solution of 54,5 g (0,5 mole) of ethylbromide in 150 ml dried diethylether was unter stirring dripped into a suspension of 12 g (0,5 mole) magnesium in form of small granules in 50 ml dried diethylether in such a manner that the mixture was slightly boiling. To the solution of Grignard reagent 53,2 g (0,35 mole) 1,5-dimethyl-bicyclo[3.2.1]octane-8-one dissolved in 70 ml dried diethylether, were added dropwise within 30 min. After 2 h of stirring at boiling temperature the mixture was allowed to cool to room temperature. Then 100 ml of saturated NH$_4$Cl solution were added, the mixture was several times extracted with ether, the combined organic phases were washed with saturated NaHCO$_3$ solution, dried over Na$_2$SO$_4$ and the solvent was distilled off under vacuum. Destillation of the residue resulted in 54 g product which consisted of 40% 2 and 60% 7. Further fine distillation resulted in 18,5 g 7 having a boiling point (1 ml) of 68° C. IR: 3500/3600 cm$^{-1}$ (O—H).—NMR (CCl₄): δ=0.88, s (1-,5-CH₂), 0,97, t, J=7 Hz (—CH₂—CH₃), 1.45 ppm, br. s (6-, 7-CH₂).—MS: m/e (%)=153 (100, M⁺-29), 135 (56), 125 (20), 123 (20), 107 (71), 99 (45), 69 (46).C₁₂H₂₂O (M=182.30).

EXAMPLE 6

1,5-dimethyl-8-isopropyl-bicyclo[3.2.1]octane-8-ol (10)

10,5 g (1,5 mole) lithium (finelly divided) and 76 g (0,5 mole) dimethylbicyclo[3.2.1]octane-8-one (4) were added to 800 ml ether (absolute). Into this mixture a solution of 92,3 g (9,75 mole) isopropylbromide in 300 ml absolute ether was dropwise added at −10° C. within 4 h. After 1 h of stirring at 40° C. the mixture was hydrolysed and processed for isolation in usual manner. By distillation over a turning band column 46 g (47%) of 10 having a boiling point (1 mm) of 76° C. resulted from the raw product. IR: 3500/3600 cm⁻¹ (O—H).—NMR (CCl₄): δ=0,91, s (1-, 5-CH₃), 1,15, d, J=7 Hz (CH₃—CH—CH₃), 1,55 ppm, br. s (6-, 7-CH₂).C₁₃H₂₄O (M=196,32)

EXAMPLE 7

(Preparation and spectrocopical data of 9, 11, 12 13 and 17)

1,5-dimethyl-8-propyl-bicyclo[3.2.1]octane-8-ol (9)

Preparation analogeous to Example 5. b.p. (1 mm) 77° C.—IR: 3500/3600 cm⁻¹ (O—H).—NMR (CCl₄): δ=0,90, s (1-, 5-CH₃) 0,93, br. t (—CH₂—CH₃) 1,48 ppm, br. s (6-, 7-CH₂).C₁₃H₂₄O (M=196,32).

8-butyl-1,5-dimethyl-bicyclo[3.2.1]octane-8-ol (11)

Preparation according to Example 4. b.p. (2 mm) 94° C. IR: 3500/3600 cm⁻¹ (O—H).—NMR (CCl₄) δ=0,90, s (1-, 5-CH₃), 0,92, br. t (—CH₂—CH₃), 1,48 ppm, br. s (6-, 7-CH₂).C₁₄H₂₆O (M=210,35)

1,5-dimethyl-8-2'-methyl-propyl-bicyclo[3.2.1]octane-8-ol (12)

Preparation according to Example 5. b.p. (1 mm) 92° C. IR: 3500/3600 cm⁻¹ (O—H).—NMR (CCl₄): δ=0,90, s (1-, 5-CH₃), 1,12, d, J=7 Hz (2'-CH₃), 1.59 ppm, br. s (6-, 7-CH₂).C₁₄H₂₆O (M=210,35)

1,5-dimethyl-8-3'-methyl-propyl-bicyclo[3.2.1]octane-8-ol (13)

Preparation according to Example 5. b.p. (1 mm) 80° C. IR: 3600 cm⁻¹ (O—H).—NMR (CCl₄): δ=0,90, s (1-, 5-CH₃), 0,98, d, J=7 Hz (3'-CH₃), 1.46 ppm, br. s (6-, 7-CH₂).C₁₅H₂₈O (M=224,37)

1,5-dimethyl-8-cyclopentyl-bicyclo[3.2.1]octane-8-ol (17)

Preparation according to Example 5. b.p. (1 mm) 112° C. IR: 3500/3600 cm⁻¹ (O—H).—NMR (CCl₄): δ=0,90, s (1-, 5-CH₃), 1.51 ppm, s (6-, 7-CH₂).C₁₅H₂₈O (M=224,37)

EXAMPLE 8 application

| Perfume oil "Eau de Cologne masculin" | |
|---|---|
| 300 g | Bergamot oil, Reggio |
| 50 g | Petitgrain oil, Paraguay |
| 200 g | Orange oil, Florida |
| 100 g | Lemon oil, Messina |
| 10 g | Nutmeg oil |
| 60 g | Rosemary oil, Spanish |
| 50 g | Litsea Cubeba oil |
| 40 g | 3-oxabicyclo [10.3.0] pentadec-6-en |
| 40 g | Calaren epoxid |
| 20 g | Coriander oil |
| 20 g | Cumarin |
| 15 g | Phenyl ethyl alcohol |
| 15 g | Thymol |
| 5 g | Cedar leaf oil, Virginia |
| 20 g | Dimethyltetrahydrobenzaldehyde 10% i. DPG* |
| 50 g | Lavender oil, French |
| 995 g | |

*DPG = Di propylene glycol

The above perfume oil is a commercial product, but its effect is somewhat unharmonious: herbal fatty-sweet aspects appear. By adding only 0.5 g of a 0.1% solution of 8-ethyl-1.5-dimethyl-bicyclo[3.2.1]octane-8-ol (7), a harmonious composition with a natural diffusion is obtained. The agrumen aspects are emphasized and the odor complex has a fresher more elegant effect.

EXAMPLE 9 application

| Perfume oil "Fougère" | |
|---|---|
| 333,0 g | Lavandin oil abrialis |
| 246,0 g | p-tert.-butylcyclohexylacetate |
| 145,0 g | Cedrol fraction (50%) |
| 45,0 g | Linalyl acetate |
| 44,0 g | Dihydromyrcenole |
| 44,0 g | Oak moss extract |
| 29,0 g | Linalool |
| 22,0 g | Cumarin |
| 22,0 g | l-Octen-e-ol, 1% |
| 22,0 g | Lavender Absolue |
| 14,0 g | Ambergris tincture, 1% in DPG |
| 9,0 g | Methylhexyl ketone, 10% in DPG |
| 7,0 g | Ethylene brassylate |
| 4,0 g | α-Ionone |
| 986,0 g | |

This perfume oil is a fougère complex with slightly heavy-sweetish aspects. After adding 0,5 g of a 0.1% solution of 8-ethyl-1,5-dimethyl-bicyclo-[3.2.1]octane-8-ol (in ethanol), it is observed that the heavy sweet notes are suppressed in favor of a distinctly intensified diffusion emphasizing fresh, woody aspects with undertones of patchouli and ambergris.

Compound I may be used as odorant in pure form; as component in perfume oils or flavor compositions, the usual concentrations ae 0.00001–30%, preferably 0.001 to 10%. All percents given herein are percents by weight.

What we claim is:

1. C-8-substituted 1,5-dimethyl-bicyclo[3.2.1]-8-ols according to general formula I

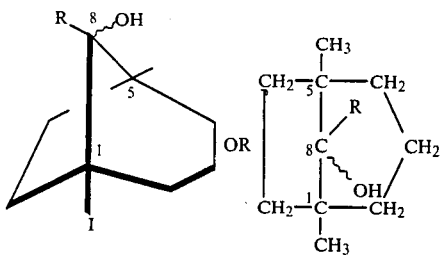

wherein R is a lower open chained or cyclic alkyl, alkenyl or alkinyl group with up to 6 preferably up to 5 carbon atoms and the wavy line at the C-8 atom means epimeric forms.

2. Compounds according to claim 1 wherein R is a straight chained alkyl group.

3. Compounds according to claim 1 wherein R is a single branched alkyl group selected from the group consisting of iso-propyl, sec.-butyl and iso-amyl.

4. Compounds according to claim 1, wherein R is an alkenyl group selected from the group consisting of vinyl, allyl and dimethylallyl.

5. Compounds according to claim 1, wherein R is the alkynyl group ethynyl or propynyl.

6. A compound as defined in claim 1 which is 1,5-dimethyl-8-vinyl-bicyclo[3.2.1]octane-8-ol.

7. A compound as defined in claim 1 which is 1.5-dimethyl-8-ethyl-bicyclo[3.2.1]octane-8-ol.

8. A compound as defined in claim 1 which is 1,5,8-trimethyl-bicyclo[3.2.1]octane-8-ol.

9. A compound as defined in claim 1 which is 1,5-dimethyl-8-isopropyl-bicyclo[3.2.1]octane-8-ol.

10. A compound as defined in claim 1 which is 1,5-dimethyl-8-propyl-bicyclo[3.2.1]octane-8-ol.

11. A compound as defined in claim 1 which is 8-butyl-1,5-dimethyl-bicyclo[3.2.1]octane-8-ol.

12. A compound as defined in claim 1 which is 1,5-dimethyl-8-2'-methyl-propyl-bicyclo[3.2.1]octane-8-ol.

13. A compound as defined in claim 1 which is 1,5-dimethyl-8-3'-methyl-propyl-bicyclo[3.2.1]octane-8-ol.

14. A compound as defined in claim 1 which is 1,5-dimethyl-8-cyclopentyl[3.2.1]octane-8-ol.

15. A compound of the formula

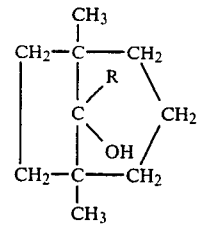

where R represents a hydrocarbon group selecting from the group consisting of alkyl, alkenyl and alkynyl having from 1-6 carbon atoms.

16. An oderiferous or perfume composition containing an active amount of a compound of the formula:

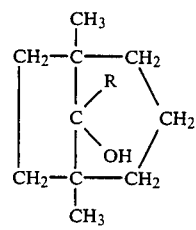

wherein R represents a hydrocarbon group selected from the group consisting of alkyl, alkenyl and alkynyl having from 1-6 carbon atoms.

* * * * *